(12) United States Patent
Conner et al.

(10) Patent No.: US 7,956,125 B2
(45) Date of Patent: Jun. 7, 2011

(54) (THIO)PHENOXY PHENYL SILANE COMPOSTION AND METHOD FOR MAKING SAME

(75) Inventors: David M. Conner, Bethlehem, PA (US); David Wayne Mosley, Philadelphia, PA (US)

(73) Assignee: Rohm and Haas Company, Philadelphia, PA (US)

( * ) Notice: Subject to any disclaimer, the term of this patent is extended or adjusted under 35 U.S.C. 154(b) by 183 days.

(21) Appl. No.: 12/220,739

(22) Filed: Jul. 28, 2008

(65) Prior Publication Data
US 2009/0039313 A1   Feb. 12, 2009

Related U.S. Application Data

(60) Provisional application No. 60/962,271, filed on Jul. 27, 2007.

(51) Int. Cl.
C08L 83/04 (2006.01)
C08L 83/00 (2006.01)
C08L 83/02 (2006.01)
C08K 3/02 (2006.01)
C08F 283/00 (2006.01)
C09K 3/00 (2006.01)

(52) U.S. Cl. ........ 524/860; 524/588; 524/789; 524/858; 524/859; 525/477; 252/182.3

(58) Field of Classification Search ................... 442/157; 524/862, 861, 858, 859, 860; 525/477, 478; 428/447, 446; 528/32
See application file for complete search history.

(56) References Cited

U.S. PATENT DOCUMENTS
3,114,759 A   12/1963   Lewis

FOREIGN PATENT DOCUMENTS
EP   1 749 861   2/2007
EP   1 927 636   6/2008

OTHER PUBLICATIONS

Breed et al., Synthesis of Bis(diethoxymethylsilyl) derivatives of 4,4'-Dibromobiphenyl, 4-Bromophenyl Ether, alpha,p-dibromotoluene, and 1,6-dibromohexane, 1960, J. Org. Chem., 25, 1198-1202.*
Langham et al., "Metalation and Halogen-Metal Interconversion Reactions of Some Halogenated Phenyl Ethers", Metalation of Halogenated Phenyl Ethers, vol. 63, Feb. 1941, pp. 545-549.
Yoshinori Yamanoi, "Palladium-Catalyzed Silylations of Hydrosilanes with Aryl Halides Using Bulky Alkyl Phosphine", J. Org. Chem., 70, 2005, pp. 9607-9609.
Lee et al., "A facile and efficient synthesis of aryltriethoxysilanes via sonochemical Barbier-type reaction", Tetrahedron Letters, 47, 2006, pp. 7085-7087.
European Search Report of corresponding European Application No. 08 16 1196 mailed Nov. 17, 2008.
Breed, L. W.; "Synthesis of bis(diethoxymethylsilyl) derivatives of 4,4'-dibromophenyl, 4-bromophenyl ether, alpha, p-dibromotoluene, and 1,6-dibromohexane"; Journal of Organic Chemistry, vol. 25, No. 7, Jul. 1960, pp. 1198-1202.

* cited by examiner

*Primary Examiner* — Ling-Siu Choi
*Assistant Examiner* — Monique Peets
(74) *Attorney, Agent, or Firm* — Jonathan D. Baskin

(57) ABSTRACT

A (thio)phenoxyphenyl phenyl silane composition is disclosed. A method of making the (thio)phenoxyphenyl phenyl silane composition is also disclosed, the method further including a step of purification. A high purity (thio)phenoxyphenyl phenyl silane composition suitable for use in the preparation of encapsulants for high brightness light emitting devices is further disclosed.

7 Claims, No Drawings

(THIO)PHENOXY PHENYL SILANE COMPOSTION AND METHOD FOR MAKING SAME

The present invention relates to a (thio)phenoxy phenyl silane composition and to a method of making that (thio)phenoxy phenyl silane composition.

There is a need for transparent high refractive index silicones for optical applications. There is also a need for thermally stable silicones. In addition, there is need for polysiloxanes and other silicon-based polymers having high refractive index, good thermal stability, and transparency which are liquid, or which form curable compositions which are liquid before curing, during some portion of curing, or both. In many cases, silicones are needed which can be cured into elastomers. In these cases, it is convenient to have liquid silicone-based precursors which can be cross-linked to form cured compositions.

High refractive index polymers are of interest for optical device encapsulation, medical optical devices such as contacts or intraocular lenses, and plastic optical components such as lenses and waveguides. In many of these cases it is desirable to cure the polymer in place using liquid silicon-containing reactants, and to use silicon-containing reactants that are high refractive index polymers, such as polysiloxanes.

High brightness LED manufacturers desire optical polymers with high transparency in the visible region, high refractive indices (i.e., refractive indices of approximately 1.60 or higher), and excellent heat stability over tens of thousands of hours of operation. Additionally the LED industry uses liquid prepolymers, which are then cured in place after much of the device is assembled. Therefore the curing polymer system must show minimal shrinkage, and must be curable under conditions which do not harm the assembled device. At this time, manufacturers employ epoxies and silicones for this purpose. However, epoxies exhibit too much yellowing for use in the new high power LED devices, which can operate at junction temperatures of 150° C. Silicones are therefore becoming the dominant encapsulant in LEDs, since some silicones exhibit excellent heat stability and little yellowing. Commercial silicone encapsulants currently have refractive indices ranging from 1.41 to 1.57.

The refractive index of the encapsulant plays an important role in determining how much light is extracted from the LED device. This is due to total, or very high, internal reflection of light as it passes from the solid-state high refractive index LED to a low index polymer medium. Typical LED devices have refractive indices of approximately 2.5. Thus, there is great interest in obtaining silicone encapsulants having higher refractive indices while maintaining excellent long term heat stability.

The refractive index of a polymer is determined by the molar refractivities of its constituent groups. Commercial silicone monomers are predominantly combinations of aliphatic groups and phenyl groups. This effectively limits the refractive index in traditional liquid silicones to an upper end of about 1.57-1.58. The refractive index of poly(diphenylsiloxane) is 1.61, but it is a solid polymer. Since many applications require liquid prepolymers, it is necessary to blend lower glass transition temperature ($T_g$) monomers with diphenylsiloxane monomers in order to obtain a liquid, leading to a reduction in the refractive index. This leads to an upper end RI of 1.57-1.58, as mentioned. What is needed is a monomer that has a similar or higher refractive index and contributes to lower $T_g$ relative to diphenylsiloxane monomers when incorporated into a cured polysiloxane composition.

U.S. Pat. No. 3,114,759 discloses aryloxyaryl aryl alkyl halosilanes which can be used as capping agents to form "chain-stopped high temperature fluid organopolysiloxanes". Unfortunately, the presence of an alkyl group as a silicon-bonded organic group of those halosilanes limits the refractive indices of the halosilanes, as well the refractive indices of polysiloxanes made using them as starting materials. In addition, those aryloxyaryl aryl alkyl halosilanes are monofunctional and, therefore, may be used only as end-capping units, limiting the extent of their incorporation into polysiloxanes.

We have discovered (thio)phenoxyphenyl phenyl silanes having Formula I,

$$Ph^2\text{-}Q\text{-}Ph^1\text{-}Si(Ph^3)(OR)_2 \quad (I),$$

wherein: $Ph^1$ is a phenyl ring having $Ph^2$-Q-, —Si-($Ph^3$)$(OR)_2$, and four hydrogen atoms as substituents; $Ph^2$-Q is a (thio)phenoxy group where $Ph^2$ is phenyl and Q is selected from oxygen atom, sulfur atom, and combinations thereof, $Ph^2$-Q is in a position on the $Ph^1$ phenyl ring which is ortho-, meta-, or para-relative to the Si atom; $Ph^3$ is phenyl; and R is a hydrogen atom or a $C_1$-$C_{10}$ hydrocarbon radical independently selected from: linear, branched, or cyclic $C_1$-$C_{10}$ alkyl; phenyl; substituted phenyl; aralkyl; and combinations thereof. We have further discovered a synthetic method that produces those (thio)phenoxyphenyl phenyl silanes in high yield. The synthetic method is further capable of producing the (thio)phenoxyphenyl phenyl silanes in very high purity, allowing them to be incorporated into cured (thio)phenoxyphenyl polysiloxane encapsulants for high brightness light emitting devices capable of long term use under harsh operating conditions.

One aspect of the present invention is directed to a (thio) phenoxyphenyl phenyl silane composition comprising a (thio)phenoxyphenyl phenyl silane having Formula I

$$Ph^2\text{-}Q\text{-}Ph^1\text{-}Si(Ph^3)(OR)_2 \quad (I)$$

wherein:
Ph$^1$ is a phenyl ring having Ph$^2$-Q-, —Si(Ph$^3$)(OR)$_2$, and four hydrogen atoms as substituents;
Ph$^2$-Q is a (thio)phenoxy group where Ph$^2$ is phenyl and Q is selected from oxygen atom, sulfur atom, and combinations thereof;
Ph$^2$-Q is in a position on the Ph$^1$ phenyl ring which is ortho-, meta-, or para-relative to the Si atom;
Ph$^3$ is phenyl; and
R is independently selected from: a hydrogen atom, a $C_1$-$C_{10}$ hydrocarbon radical, and combinations thereof, wherein the $C_1$-$C_{10}$ hydrocarbon radical is independently selected from: linear, branched, or cyclic $C_1$-$C_{10}$ alkyl; phenyl; substituted phenyl; aralkyl; and combinations thereof.

A second aspect of the present invention is directed to a method of making the (thio)phenoxyphenyl phenyl silane composition of claim 1, comprising the steps of:
A. providing a (thio)phenoxyphenyl halide having Formula II

$$Ph^2\text{-}Q\text{-}Ph^1\text{-}X \quad (II)$$

wherein:
Ph$^1$ is a phenyl ring having Ph$^2$-Q-, X and four hydrogen atoms as substituents;
Ph$^2$-Q is a (thio)phenoxy group where Ph$^2$ is phenyl and Q is selected from oxygen atom, sulfur atom, and combinations thereof;

Ph²-Q is in a position on the Ph¹ phenyl ring which is ortho-, meta-, or para-relative to X; and X is a halide selected from Cl, Br, and combinations thereof;

B. providing a phenyl trioxy silane having Formula III

$$Ph^3\text{-}Si(OR)_2(OR') \quad (III)$$

wherein:

each R is a hydrogen atom or a $C_1$-$C_{10}$ hydrocarbon radical independently selected from: linear, branched, or cyclic $C_1$-$C_{10}$ alkyl; phenyl; substituted phenyl; aralkyl; and combinations thereof; and R' is a $C_1$-$C_{10}$ hydrocarbon radical independently selected from: linear, branched, or cyclic $C_1$-$C_{10}$ alkyl; phenyl; substituted phenyl; aralkyl; and combinations thereof;

C. reacting the (thio)phenoxyphenyl halide with an active metal reagent comprising metal atom M to form a (thio)phenoxyphenyl metal intermediate having formula IV

$$Ph^2\text{-}Q\text{-}Ph^1\text{-}M\text{-}X_n \quad (IV)$$

wherein:

M is selected from magnesium and lithium;

X is selected from Cl, Br, and combinations thereof; and n=0 or 1; and

D. reacting the (thio)phenoxyphenyl metal intermediate with the phenyl trioxy silane to form the (thio)phenoxyphenyl phenyl silane.

The terminology of this specification includes words specifically mentioned herein, derivatives thereof, and words of similar import.

Used herein, the following terms have these definitions:

The words "a" and "an" as used in the specification mean "at least one", unless otherwise specifically stated.

"Range". Disclosures of ranges herein take the form of lower and upper limits. There may be one or more lower limits and, independently, one or more upper limits. A given range is defined by selecting one lower limit and one upper limit. The selected lower and upper limits then define the boundaries of that particular range. All ranges that can be defined in this way are inclusive and combinable, meaning that any lower limit may be combined with any upper limit to delineate a range. For example, if ranges of 60 to 120 and 80 to 110 are recited for a particular parameter, it is understood that the ranges of 60 to 110 and 80 to 120 are also contemplated. Additionally, if minimum range values of 1 and 2 are recited, and if maximum range values of 3, 4, and 5 are recited, then the following ranges are all contemplated: 1 to 3, 1 to 4, 1 to 5, 2 to 3, 2 to 4, and 2 to 5.

The term "ppm" means "parts per million" which, in turn, means "weight parts per million weight parts". Parts per million are weight based. Therefore, the amount of a given component x in a composition y is calculated by dividing the weight of component x by the weight of composition y and then multiplying by one million. For example, if 0.005 gram of impurity X is present in 100 grams of a (thio)phenoxyphenyl phenyl silane of the present invention, then impurity X is present at 50 ppm, based on the total weight of the (thio)phenoxyphenyl phenyl silane. Further, if 0.002 g of impurity Y and 0.0001 g of impurity Z are also present, then the corresponding ppm values are, respectively, 20 ppm and 1 ppm.

Purities and impurity levels are expressed as weight percent ("weight %"; "wt %"). Analytical determination of purity levels is accomplished using GC-FID as described in the experimental section infra. The CG-FID method provides results based on the area percents for each eluted peak. Due to the similarity of compound compositions in this GC-FID analysis, the area % results for the peaks represent good estimates of weight percents (weight %s). Weight percent values are, therefore, equated to area percent values herein.

A "silicon bonded organic group" is an organic group bonded to a silicon atom, wherein an "organic group" contains at least one carbon, or is a hydrogen atom or hydroxy group.

A "silicon bonded phenoxyphenyl group" is a silicon bonded phenyl group having a carbon atom of that phenyl ring directly bonded to a silicon atom and another carbon of the same phenyl ring directly bonded to an oxygen atom of a "phenoxy substituent". That oxygen atom of the phenoxy substituent is therefore an "ether linkage" (i.e., a "diphenyl ether linkage") of the silicon bonded phenoxyphenyl group. A "silicon bonded thiophenoxy phenyl group" is a silicon bonded phenyl group having a carbon atom of that phenyl ring directly bonded to a silicon atom and another carbon of the same phenyl ring directly bonded to a sulfur atom of a "thiophenoxy substituent". The term "(thio)phenoxy" includes both "phenoxy" and "thiophenoxy". The term "silicon bonded (thio)phenoxyphenyl" includes both "silicon bonded phenoxyphenyl" and "silicon bonded thiophenoxyphenyl".

A "hydrocarbon radical" is a group consisting of carbon atoms and hydrogen atoms. The hydrocarbon radical of the present invention is selected from $C_1$-$C_{10}$ hydrocarbon radicals.

A "(thio)phenoxyphenyl phenyl silane" is a silane having Formula I

$$Ph^2\text{-}Q\text{-}Ph^1\text{-}Si(Ph^3)(OR)_2 \quad (I)$$

wherein:

Ph¹ is a phenyl ring having Ph²-Q-, —Si(Ph³)(OR)₂, and four hydrogen atoms as substituents;

Ph²-Q is a (thio)phenoxy group where Ph² is phenyl and Q is selected from oxygen atom, sulfur atom, and combinations thereof;

Ph²-Q is in a position on the Ph¹ phenyl ring which is ortho-, meta-, or para-relative to the Si atom;

Ph³ is phenyl; and

R is independently selected from: a hydrogen atom (alternatively "hydrogen" or "H"), a $C_1$-$C_{10}$ hydrocarbon radical, and combinations thereof, wherein the $C_1$-$C_{10}$ hydrocarbon radical is independently selected from: linear, branched, or cyclic $C_1$-$C_{10}$ alkyl; phenyl; substituted phenyl; aralkyl; and combinations thereof.

Each R may further be, independently, selected from: hydrogen atom, methyl, ethyl, iso-propyl, phenyl, and combinations thereof. Each R may still further be, independently, selected from: hydrogen atom, methyl, ethyl, and combinations thereof. Each R may yet further be, independently, selected from hydrogen atom, methyl, and combinations thereof. R may also be methyl.

The (thio)phenoxyphenyl phenyl silanes of the present invention, therefore, include: (thio)phenoxyphenyl phenyl dialkoxy silanes wherein each R-group is, independently, a $C_1$-$C_{10}$ hydrocarbon radical which is linear, branched, or cyclic, such as phenoxyphenyl phenyl dimethoxy silane, thiophenoxyphenyl phenyl dimethoxy silane, (thio)phenoxyphenyl phenyl diethoxy silane, (thio)phenoxyphenyl phenyl di-(iso-propoxy) silane, (thio)phenoxyphenyl phenyl cyclohexyloxy methoxy silane, and (thio)phenoxyphenyl phenyl ethoxy methoxy silane; (thio)phenoxyphenyl phenyl diphenoxy silanes wherein each R-group phenyl is, independently, unsubstituted or substituted with alkyl groups having a combined total of one to four carbons, such as (thio)phenoxyphenyl phenyl diphenoxy silane, and (thio)phenoxyphenyl phenyl di(p-tolyloxy) silane; (thio)phenoxyphenyl phenyl di(aralkyl) silanes wherein each aralkyl R-group has, independently, a combined total of one to four alkyl carbon atoms, one to four of which are included in the bridging alkyl segment between the phenyl group and the silicon atom, and zero to three of which may be included in further alkyl substituents of the phenyl ring, such as (thio)phenoxyphenyl phenyl di(2-phenylethoxy) silane, (thio)phenoxyphenyl phenyl di(2-p-tolylethoxy silane); and (thio)phenoxyphenyl phenyl 2-phenylethoxy 2-p-tolylethoxy silane; and (thio)phenoxyphenyl phenyl dihydroxy silane. The (thio)phenoxyphenyl phenyl silanes of the present invention further include combinations of R-groups selected from more than one of the above R-group categories, for example: (thio)phenoxyphenyl phenyl hydroxy methoxy silane; (thio)phenoxyphenyl phenyl ethoxy hydroxy silane; (thio)phenoxyphenyl phenyl ethoxy phenoxy silane; (thio)phenoxyphenyl phenyl methoxy phenoxy silane; and (thio)phenoxyphenyl phenyl methoxy 2-phenylethoxy silane. It is further understood that, for any of these types of (thio)phenoxyphenyl phenyl silane, the (thio)phenoxyphenyl group may be an ortho-(thio)phenoxyphenyl, a meta-(thio)phenoxyphenyl, a para-(thio)phenoxyphenyl, or combinations thereof. The (thio)phenoxyphenyl phenyl silane of the present invention may further be selected from any of the types of phenoxyphenyl phenyl silanes just enumerated, and combinations thereof. The (thio)phenoxyphenyl phenyl silane of the present invention may still further be selected from any of the types of thiophenoxyphenyl phenyl silanes just enumerated, and combinations thereof. The (thio)phenoxy phenyl silane of the present invention may also be selected from combinations of phenoxyphenyl phenyl silanes and thiophenoxyphenyl phenyl silanes.

"Structure A", "structure B", and "structure C" infra are the Formula I structures when $Ph^2$-Q-$Ph^1$- is a (thio)phenoxyphenyl group [Q is an oxygen atom or a sulfur atom] which is, respectively, ortho-(thio)phenoxyphenyl, meta-(thio)phenoxyphenyl, and para-(thio)phenoxyphenyl relative to the position of attachment of the silicon group of the (thio)phenoxyphenyl phenyl silane of the present invention.

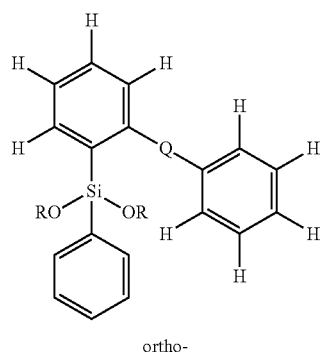

ortho-

Structure A

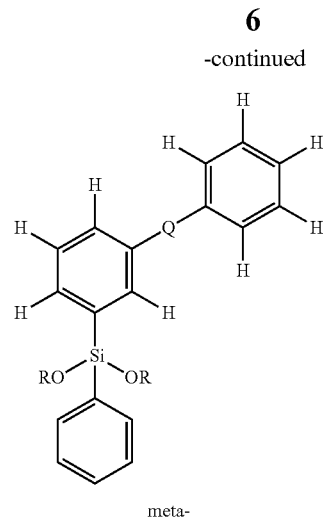

meta-

Structure B

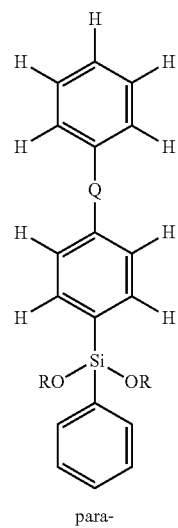

para-

Structure C

Formula I Structures A, B, and C

A "(thio)phenoxyphenyl phenyl silane composition" includes a (thio)phenoxyphenyl phenyl silane of the present invention. The (thio)phenoxyphenyl phenyl silane composition of the present invention is a composition including a (thio)phenoxyphenyl phenyl silane having Formula I present in any amount. Typically, a (thio)phenoxyphenyl phenyl silane composition recovered from a reaction mixture after a reaction to prepare a (thio)phenoxyphenyl phenyl silane will contain a (thio)phenoxyphenyl phenyl silane in an amount of: at least 80 percent by weight; and no more than 99.90 percent by weight, based on the weight of the (thio)phenoxyphenyl phenyl silane composition.

When it is desired to use the (thio)phenoxyphenyl phenyl silane composition of the present invention in the preparation of a cured (thio)phenoxy phenyl polysiloxane composition that will be suitable as an encapsulant for a light emitting device such as a light emitting diode (LED), the amount of (thio)phenoxyphenyl phenyl silane having Formula I in the phenoxyphenyl phenyl silane composition after purification and absent any diluents is: at least 99.0, at least 99.5, or at least 99.9 percent by weight; and equal to or less than 100, no more than 99.999, no more than 99.998 percent by weight, based on the weight of the (thio)phenoxyphenyl phenyl silane composition.

Further, when it is desired to use the (thio)phenoxyphenyl phenyl silane composition of the present invention in the preparation of a cured (thio)phenoxy phenyl polysiloxane composition that will be suitable as an encapsulant for a light emitting device such as a high brightness LED (HBLED) capable of passing the accelerated heat aging test infra, the amount of (thio)phenoxyphenyl phenyl silane having Formula I in the (thio)phenoxyphenyl phenyl silane composition after purification and absent any diluents is: at least 98, at least 99, at least 99.5, or at least 99.9 percent by weight; and equal to or less than 100, no more than 99.999, no more than 99.998 percent by weight, based on the weight of the (thio)phenoxyphenyl phenyl silane composition.

A "(thio)phenoxyphenyl halide" (alternatively "halo (thio) phenoxy benzene") is a phenyl halide having Formula II $$Ph^2\text{-}Q\text{-}Ph^1\text{-}X \qquad (II)$$

wherein:

$Ph^1$ is a phenyl ring having $Ph^2$-Q, X and four hydrogen atoms as substituents;

$Ph^2$-Q is a (thio)phenoxy group where $Ph^2$ is phenyl and Q is selected from oxygen atom, sulfur atom, and combinations thereof;

$Ph^2$-Q is in a position on the $Ph^1$ phenyl ring which is ortho-, meta-, or para-relative to X; and X is a halide selected from Cl, Br, and combinations thereof.

"Structure D", "structure E", and "structure F" infra are the Formula II structures when the (thio)phenoxyphenyl group $Ph^2$-Q-$Ph^1$- is, respectively, ortho-(thio)phenoxyphenyl, meta-(thio)phenoxyphenyl, and para-(thio)phenoxyphenyl relative to the position of attachment of the halide atom of $Ph^1$. $R^1$, $R^2$, $R^3$, $R^4$, and $R^5$ are all hydrogen.

Formula II structures D, E, and F

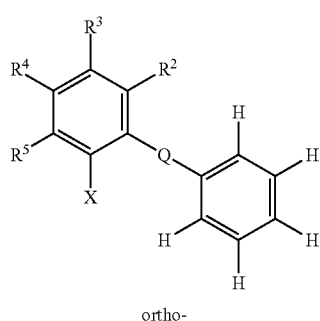

Structure D ortho-

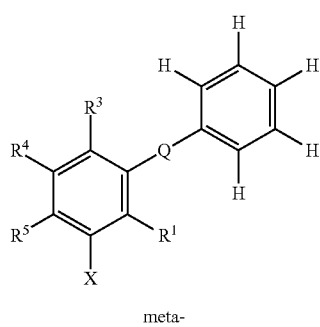

Structure E meta-

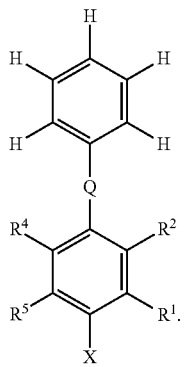

Structure F para-

When a (thio)phenoxyphenyl halide represented by Formula II is used as a starting material in the preparation of a (thio)phenoxyphenyl phenyl silane of the present invention, it may be utilized as a single isomer (i.e., either ortho-, meta-, or para-) or as any combination of the ortho-, meta-, and para isomers. The halide of any of the isomers of a (thio)phenoxyphenyl halide may further be selected from chloride, bromide, and combinations thereof.

The (thio)phenoxyphenyl halide represented by Formula II may be present in the (thio)phenoxyphenyl phenyl silane composition of the present invention. When the (thio)phenoxyphenyl phenyl silane composition is to be utilized in further reactions to produce intermediates and/or final products, the presence of a (thio)phenoxyphenyl halide in that (thio)phenoxyphenyl phenyl silane composition may or may not be well tolerated by those intermediates, those final products, or the performance conditions to which those final products, alone or in combination with other products or articles, are subjected. When the presence of a (thio)phenoxyphenyl halide in a (thio)phenoxyphenyl phenyl silane composition is well tolerated, the (thio)phenoxyphenyl halide having Formula II may be present in an amount of: 0 or greater, at least 0.0001, at least 0.0005, at least 0.001, or at least 0.005 percent by weight; and no more than 10, no more than 5, no more than 1, no more than 0.1, or no more than 0.01 percent by weight, based on the weight of the (thio)phenoxyphenyl phenyl silane composition.

When it is desired to use the (thio)phenoxyphenyl phenyl silane composition of the present invention in the preparation of a cured (thio)phenoxyphenyl phenyl polysiloxane composition (i.e., wherein the(thio)phenoxyphenyl phenyl silane composition is used as a component of a curable composition or a as a precursor to a component of a curable composition) that will be suitable as an encapsulant for a light emitting device such as a light emitting diode (LED), the amount of (thio)phenoxyphenyl halide having Formula II in the (thio) phenoxyphenyl phenyl silane composition after purification is: equal to or greater than 0, at least 0.5, at least 1, at least 5, or at least 10 ppm; and no more than 1000, no more than 500, no more than 100, or no more than 50 ppm, based on the weight of the (thio)phenoxyphenyl phenyl silane composition.

Further, when it is desired to use the (thio)phenoxyphenyl phenyl silane composition of the present invention in the preparation of a cured (thio)phenoxyphenyl phenyl polysiloxane composition (i.e., wherein the(thio)phenoxyphenyl phenyl silane composition is used as a component of a curable composition or a as a precursor to a component of a curable composition) that will be suitable as an encapsulant that can withstand temperatures of 150-200° C. for a light emitting device such as a high brightness LED (HBLED), the amount of (thio)phenoxyphenyl phenyl halide having Formula II in the (thio)phenoxyphenyl phenyl silane composition after purification is: equal to or greater than 0, at least 0.001, at least 0.1, at least 0.5, or at least 1 ppm; and no more than 500, no more than 200, no more than 100, no more than 50, or no more than 20 ppm, based on the weight of the (thio)phenoxyphenyl phenyl silane composition.

The (thio)phenoxyphenyl phenyl silane composition of the present invention can be made by a process including the steps of:

A. providing a (thio)phenoxyphenyl halide having Formula II

Ph²-Q-Ph¹-X            (II)

wherein:
  Ph² is a phenyl ring having Ph²-Q-, X and four hydrogen atoms as substituents;
  Ph²-Q is a (thio)phenoxy group where Ph² is phenyl and Q is selected from oxygen atom, sulfur atom, and combinations thereof;
  Ph²-Q is in a position on the Ph¹ phenyl ring which is ortho-, meta-, or para-relative to X; and
  X is a halide selected from Cl, Br, and combinations thereof;

B. providing a phenyl trioxy silane having Formula III

Ph³-Si(OR)₂(OR')            (III)

wherein:
  R is a hydrogen atom or a $C_1$-$C_{10}$ hydrocarbon radical independently selected from: linear, branched, or cyclic $C_1$-$C_{10}$ alkyl; phenyl; substituted phenyl; aralkyl; and combinations thereof; and
  R' is a $C_1$-$C_{10}$ hydrocarbon radical independently selected from: linear, branched, or cyclic $C_1$-$C_{10}$ alkyl; phenyl; substituted phenyl; aralkyl; and combinations thereof;

C. reacting the (thio)phenoxyphenyl halide with an active metal reagent comprising metal atom M to form a (thio)phenoxyphenyl metal intermediate having formula IV

Ph²-Q-Ph¹-M-X$_n$            (IV)

wherein:
  M is selected from magnesium and lithium;
  X is selected from Cl, Br, and combinations thereof; and
  n=0 or 1; and D. reacting the (thio)phenoxyphenyl metal halide intermediate with the phenyl trioxy silane to form the (thio)phenoxyphenyl phenyl silane.

Suitable active metal reagents include, but are not limited to, magnesium metal, alkyl magnesium halides such as methyl magnesium iodide, and alkyl lithium compounds such as methyl lithium. For example, catalytic amounts of methyl iodide may be included in a reaction mixture containing the (thio)phenoxyphenyl halide of the present invention and magnesium. The methyl iodide and the magnesium metal react facilely to form the catalytic amount of methyl magnesium iodide which exchanges with the (thio)pheoxyphenyl halide to form a (thio)phenoxyphenyl magnesium halide capable of further reaction with the phenyl trioxy silane to form the (thio)phenoxyphenyl phenyl silane of the present invention.

A suitable approach to making the (thio)phenoxyphenyl phenyl silane of the present invention is a "one-pot" sonochemical Barbier-type reaction in which a (thio)phenoxyphenyl halide, magnesium metal, and a phenyl trialkoxy silane are combined in an anhydrous ether solvent, typically in the presence of a trace of methyl iodide. Sonication, with the formation of a (thio)phenoxyphenyl magnesium halide, produces the (thio)phenoxyphenyl phenyl silane of the present invention. A reaction scheme illustrative of this approach follows for the reaction of p-phenoxyphenyl bromide (alternatively, 4-phenoxyphenyl bromide) with magnesium metal and phenyl trimethoxy silane to produce p-phenoxyphenyl phenyl dimethoxy silane.

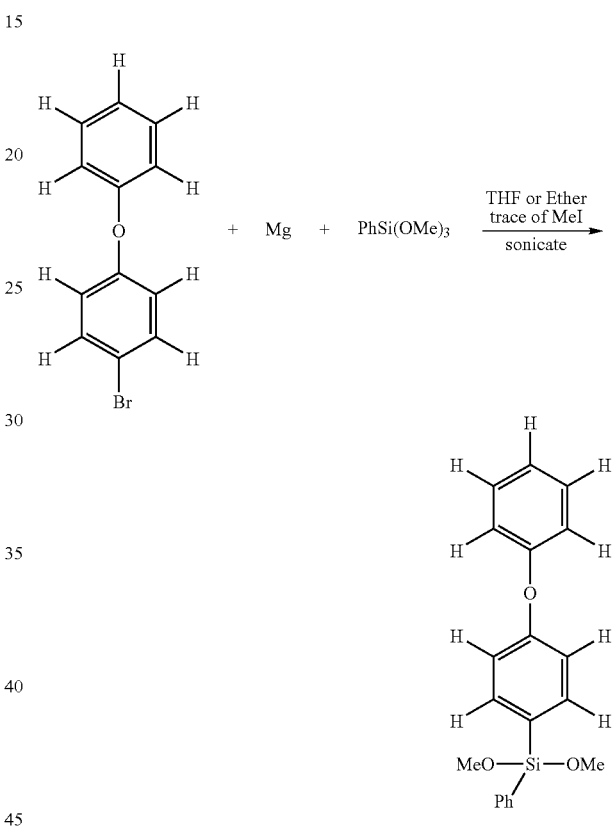

Those skilled in the art will appreciate that the order of reagent addition, the exclusion of water and oxygen, the purity of solvents and reagents, the time, temperature, and agitation of the reaction, and the method of activating the magnesium metal can all affect the reaction yield. For instance, experimental conditions, including yield enhancement through variation of the order of reagent addition, for the conversion of a variety of aryl bromides to aryl triethoxy silanes using the sonochemical Barbier-type reaction are disclosed by Lee, A. S.-Y., et al., *Tetrahedron Letters* 2006 47, 7085-7087.

Another suitable approach to making the (thio)phenoxyphenyl phenyl silane of the present invention is the sequential formation of a Grignard reagent [a (thio)phenoxyphenyl magnesium halide] followed by introduction of a phenyl trialkoxy silane. A reaction scheme illustrative of this approach follows in which p-phenoxyphenyl bromide is reacted with magnesium metal to form p-phenoxyphenyl magnesium bromide. The p-phenoxyphenyl magnesium bromide intermediate is then reacted with phenyl trimethoxy silane to produce p-phenoxyphenyl phenyl dimethoxy silane. Typically, this Grignard approach is carried out in an anhydrous ether solvent such as tetrahydrofuran ("THF") or diethyl ether.

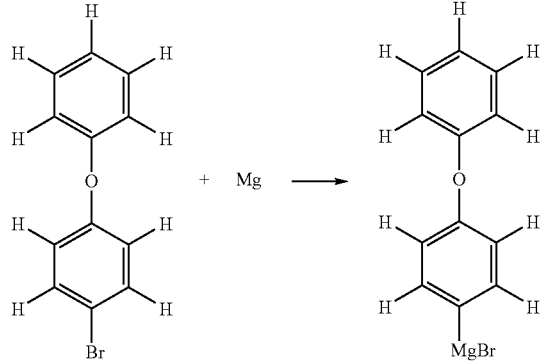

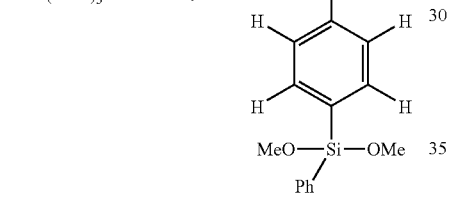

The practitioner will appreciate that the order of reagent addition, the exclusion of water and oxygen, the purity of solvents and reagents, the time, temperature, and agitation of the reaction, and the method of activating the magnesium metal can all affect the reaction yield. For example, in order to prevent addition of two Grignard moieties to one molecule of phenyltrimethoxy silane, it is desirable to slowly add Grignard reagent to a solution of at least one equivalent of phenyltrimethoxysilane. If there is an excess of phenoxyphenyl Grignard reagent present relative to phenyltrimethoxysilane, then it is more likely that bis(phenoxyphenyl) phenylmethoxysilane will be produced.

A further suitable approach to making the (thio)phenoxyphenyl phenyl silane of the present invention is the sequential formation of a (thio)phenoxyphenyl lithium by reacting a (thio)phenoxyphenyl phenyl halide with an alkyl lithium at low temperature (approximately −76° C.) in an anhydrous ether solvent to form a (thio)phenoxyphenyl lithium, followed by introduction of a phenyl trialkoxy silane to form the (thio)phenoxyphenyl phenyl silane. A reaction scheme illustrative of this approach follows in which p-phenoxyphenyl bromide is reacted with n-butyl lithium to form p-phenoxyphenyl lithium. The p-phenoxyphenyl lithium intermediate is then reacted with phenyl trimethoxy silane to produce p-phenoxyphenyl phenyl dimethoxy silane.

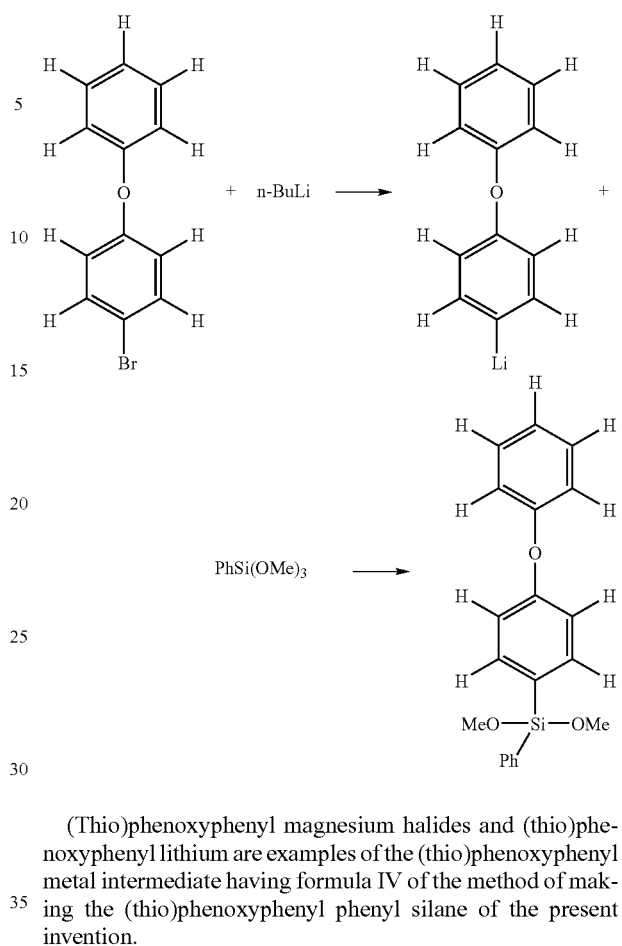

(Thio)phenoxyphenyl magnesium halides and (thio)phenoxyphenyl lithium are examples of the (thio)phenoxyphenyl metal intermediate having formula IV of the method of making the (thio)phenoxyphenyl phenyl silane of the present invention.

Another method of making the (thio)phenoxyphenyl phenyl silane of the present invention is the metal catalyzed coupling of aryl chlorides, bromide, iodides, or combinations thereof with hydridosilanes. In this case, a catalytic amount of an organometallic complex of palladium or rhodium is reacted with a phenoxyphenyl halide in the presence of a suitably substituted silane species, such as phenyldimethoxysilane which contains a single Si—H bond. The conditions for this class of couplings are known in the art. See, for example, Y. Yamanoi, *J. Org. Chem.* 70 (2005), 9607-9609, and references therein. A wide variety of phosphine ligands, arsine ligands, amine ligand, and combinations thereof, can be used to control the activity of the metal catalytic center for the reaction. In one suitable approach, aryl phosphine ligands are used to exert that control.

Work-up of reaction mixtures produced by the method of making the (thio)phenoxyphenyl phenyl silane of the present invention may be achieved by any technique known to one of skill in the art. A suitable illustrative approach includes washing the reaction mixture with an aqueous wash medium, and then concentrating the extracted organic phase [usually the reaction solvent, e.g., diethyl ether or tetrahydrofuran containing the (thio)phenoxyphenyl phenyl silane] by removal of solvent under reduced pressure. The (thio)phenoxyphenyl phenyl silane is then subjected to short-path distillation resulting in 99 weight % purity for the (thio)phenoxyphenyl phenyl silane as determined by GC-FID analysis. Further purification is achieved by column distillation. For example, approximately 300 grams of p-phenoxyphenyl phenyl dimethoxy silane having a purity of 99 weight percent is placed in a 500 mL round bottom flask equipped with a spin-bar stirrer. The round bottom flask is fitted with a 40 tray vacuum insulated distillation column equipped with a thermometer. The pressure is reduced to 0.2 mm of mercury, and the contents of the round bottom flask are heated. Once the vapor temperature reaches 170° C., the distillate is collected. This column distillation approach is capable of preparing p-phenoxyphenyl phenyl dimethoxy silane in a purity of greater than 99.95 percent by weight as determined by GC-FID. This column distillation approach is further capable of reducing the amount of p-phenoxyphenyl phenyl halide to less than 0.02 percent by weight (less than 200 ppm), based on the weight of the phenoxyphenyl phenyl dimethoxy silane as determined by GC-FID. The practitioner will recognize that still further purification may be achieved by increasing the number of trays (and, therefore, the number of theoretical plates) of the distillation column beyond 40, by employing a reflux splitting process, by repeated column distillations, and by techniques such as preparative high pressure liquid chromatography.

The terms "mole percent" and "mol %" are used interchangeably throughout. The "mol % of silicon bonded (thio)phenoxyphenyl groups" for a given silicon compound, for example a polysiloxane or a silane, is the number of moles of silicon bonded (thio)phenoxyphenyl groups contained in that silicon compound, divided by the number of moles of all silicon bonded organic groups. For example, a silicon-based precursor (see definition infra) having 4 silicon bonded (thio)phenoxyphenyl groups, 4 silicon bonded phenyl groups, and 2 silicon bonded methoxy groups, for a total of 10 silicon bonded organic groups, contains 40 mol % silicon bonded (thio)phenoxyphenyl groups, 40 mol % silicon bonded phenyl groups, and 20 mol % silicon bonded methoxy groups, based on total silicon bonded organic groups of the silicon-based precursor.

Polysiloxanes are described in the art by categorizing units, termed "primary siloxane units", based on the pattern of attachment of silicon atoms, through an intervening oxygen atom, to adjacent silicon atoms. Primary siloxane units have a single silicon atom wherein that silicon atom is bound to four substituents, one or more of which is an oxygen which is further bound directly to another silicon atom. As such, each of these two silicon atoms shares that oxygen with the other silicon atom. For example, $(CH_3)_3Si\text{—}O\text{—}Si(CH_3)_2OH$ is a polysiloxane having two primary siloxane units, each of which has a single silicon atom bound to an oxygen atom wherein that oxygen atom is bound to the silicon atom of the other primary siloxane unit. The oxygen of the hydroxy group is not bound to a second silicon atom and, as such, is not counted as a second oxygen atom for the purpose of determining if the primary siloxane unit to which it belongs is an M-unit or a D-unit (see infra). Therefore, the hydroxy group is treated as a silicon bonded organic group and the primary siloxane unit to which it belongs is an M-unit.

The term "M-unit" refers to a primary siloxane unit of a polysiloxane, wherein the silicon of that unit is attached to single, immediately adjacent, —O—Si— moiety through a covalent bond to the oxygen atom of that —O—Si— moiety.

Similarly, the terms "D-unit", "T-unit", and "Q-unit" refer, respectively, to a primary siloxane unit of a siloxane, wherein the silicon of that unit is attached to two, three, or four immediately adjacent —O—Si— moieties through a covalent bond to the oxygen atom of each of those —O—Si— moieties.

The (thio)phenoxyphenyl phenyl silane composition of the present invention can be used as a starting material for the preparation of a "silicon-based precursor component" ("silicon-based precursor") which contains a (thio)phenoxyphenyl phenyl primary siloxane unit. That silicon-based precursor component which contains a (thio)phenoxyphenyl phenyl primary siloxane unit derived from the (thio)phenoxyphenyl phenyl silane of the present invention may further be utilized as a component of a curable (thio)phenoxyphenyl phenyl silicon composition. Further, the (thio)phenoxyphenyl phenyl silane composition may also be utilized as a component of a curable (thio)phenoxyphenyl phenyl silicon composition. Curing of the curable (thio)phenoxyphenyl phenyl silicon composition, in turn, forms a cured (thio)phenoxyphenyl phenyl polysiloxane composition. U.S. provisional patent application 60/872,094 discloses the silicon-based precursor component, the curable (thio)phenoxyphenyl phenyl silicon composition, and the cured (thio)phenoxyphenyl phenyl polysiloxane composition, and further discloses methods of making all of them.

A silicon-based precursor component that can be made using the (thio)phenoxyphenyl phenyl silane composition of the present invention as a starting material is represented by average compositional formula, Formula V,

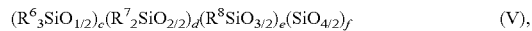

$$(R^6{}_3SiO_{1/2})_c(R^7{}_2SiO_{2/2})_d(R^8SiO_{3/2})_e(SiO_{4/2})_f \qquad (V),$$

wherein:

$R^6{}_3SiO_{1/2}$, $R^7{}_2SiO_{2/2}$, $R^8SiO_{3/2}$, and $SiO_{4/2}$ are, respectively, an M-unit, a D-unit, a T-unit, and a Q-unit, all of which are primary siloxane units;

subscripts c, d, e, and f are selected to conform with the mole fraction of $R^6{}_3SiO_{1/2}$, $R^7{}_2SiO_{2/2}$, $R^8SiO_{3/2}$, and $SiO_{4/2}$, respectively;

$0.001 \leq c \leq 1$; $0 \leq d \leq 0.999$; $0 \leq e \leq 0.50$; $0 \leq f \leq 0.10$; and $c+d+e+f=1$; and wherein:

$R^6$, $R^7$, and $R^8$ each, independently, include a silicon bonded organic group selected from alkenyl, hydrogen atom, phenyl, alkyl, hydroxy, alkoxy, phenoxy, phenoxyphenyl, thiophenoxy, thiophenoxyphenyl, other hydrocarbon radical, and combinations thereof;

at least two of the silicon bonded groups of combined $R^6$, $R^7$, and $R^8$ are silicon bonded groups selected from alkenyl, hydrogen atom, alkoxy, and combinations thereof;

the silicon bonded alkenyl group is present in the silicon in an amount of 0 mole percent to no more than 60 mole percent, based on total moles of the silicon bonded organic groups of the silicon precursor component;

the silicon bonded hydrogen atom in the silicon in an amount of 0 mole percent to no more than 60 mole percent, based on total moles of the silicon bonded organic groups of the silicon precursor component; and at least one primary siloxane unit comprises both (thio)phenoxyphenyl and phenyl as the silicon bonded organic group.

This silicon-based precursor component of Formula V, which includes at least one (thio)phenoxyphenyl phenyl silane unit as a polymerized unit, may be formed using the (thio)phenoxyphenyl phenyl silane composition of the present invention as the sole polymerizable unit. Alternatively, it may be desired to further include polymerizable units other than the (thio)phenoxyphenyl phenyl silane of the present invention.

The silicon-based precursor component of Formula V, which includes at least one (thio)phenoxyphenyl phenyl silane unit as a polymerized unit, may be utilized as a component of a curable (thio)phenoxyphenyl phenyl silicon composition. That curable (thio)phenoxyphenyl phenyl silicon composition may, optionally, further include: a silicon-based precursor component having Formula V which does not include a primary siloxane unit derived from the (thio)phenoxyphenyl phenyl silane of the present invention; hydrosilation catalyst; other polymerization catalysts, and a "capping agent" having Formula VI,

$$R^9{}_4Si \quad (VI),$$

wherein $R^9$ includes a silicon bonded organic group selected from alkenyl, hydrogen atom, phenyl, alkyl, hydroxy, alkoxy, phenoxy, phenoxyphenyl, thiophenoxy, thiophenoxyphenyl, other hydrocarbon radical, and combinations thereof.

The curable (thio)phenoxyphenyl phenyl silicon composition can be cured to form a cured (thio)phenoxyphenyl phenyl polysiloxane composition using methods disclosed in U.S. provisional patent application 60/872,094. The cured (thio)phenoxyphenyl phenyl polysiloxane composition of the present invention has many uses, including underfiller, protective coating agent, potting agent, or adhesive agent (e.g., die-bonding applications) for electric and electronic products, including semiconductors. There is no particular limit to the types of semiconductor that can be encapsulated. For example, light emitting diode (LED) devices can be encapsulated with the cured (thio)phenoxyphenyl phenyl polysiloxane composition. The high light transmittance of the cured (thio)phenoxyphenyl phenyl polysiloxane composition makes it particularly suitable for use as an underfiller, protective coating agent, potting agent, or adhesive agent in semiconductor elements used for optical applications. The (thio)phenoxyphenyl phenyl silicon moiety can be of great utility in the field of contact and intraocular lenses. Maintaining the proper glass transition temperature ($T_g$) is a critical technical constraint of intraocular and contact lenses, but high transparency and refractive index is also desired. The cured (thio)phenoxyphenyl phenyl polysiloxane composition is useful for these applications due to it's high RI and low $T_g$. Low viscosity curable (thio)phenoxyphenyl phenyl silicon compositions are useful for casting and molding lenses, including ophthalmic lenses, intraocular implants, contact lenses, and optical device lenses. Cured (thio)phenoxyphenyl phenyl polysiloxane compositions may also be used as high thermal conductivity heat transfer underfills for flip chip packaging.

The refractive index of the curable (thio)phenoxyphenyl phenyl silicon composition of the present invention is: at least 1.50, at least 1.55, or at least 1.58; and no more 1.66, no more than 1.63, no more than 1.62. These limits for refractive index are limits in the absence of high RI additives such as high RI nanoparticles.

The refractive index of the cured (thio)phenoxyphenyl phenyl polysiloxane composition of the present-invention is: at least 1.50, at least 1.55, or at least 1.58; and no more 1.66, no more than 1.63, no more than 1.62. These limits for refractive index are limits in the absence of high RI additives such as high RI nanoparticles.

When the (thio)phenoxyphenyl phenyl silane composition of the present invention is incorporated, as a polymerized unit, into a cured (thio)phenoxy phenyl polysiloxane composition which can be usefully employed as an encapsulant for high brightness light emitting devices (HBLEDs), the purity of the (thio)phenoxyphenyl phenyl silane composition must be high to avoid degradation during extended use at high temperatures. In such case, the cured (thio)phenoxy phenyl polysiloxane composition must be stable for extended time periods (e.g., thousands of hours) at use temperatures of 100° C. to 130° C., or even higher, in air. A test of the capability of a cured (thio)phenoxyphenyl phenyl polysiloxane to perform without loss of properties is the "accelerated heat aging test". A cured (thio)phenoxyphenyl phenyl polysiloxane composition that passes the accelerated heat aging test does not discolor during at least 3 days of heat aging at 200° C. in air, as indicated by a CIE b value, determined using CIE 1976 Lab $D_{65}$(illumination angle)/10(observation angle) color test method (see Experimental section, including Table 2 infra). The CIE b value increases as a material becomes more yellow, and can be used to quantify the appearance of yellow in a clear sample. Onset and extent of discoloration may also be determined by visual inspection (see Table 1 infra).

Members of a series of cured (thio)phenoxyphenyl phenyl polysiloxane compositions, each prepared using a silicon-based precursor component itself prepared using the (thio)phenoxyphenyl phenyl silane composition of the present invention, exhibit dramatic improvement in resistance to degradation of optical properties (e.g., greatly reduced yellowing) as the level of (thio)phenoxy phenyl halide in the (thio)phenoxyphenyl phenyl silane composition is reduced. Based on observations made using the accelerated heat aging test, the level of (thio)phenoxyphenyl phenyl silane contained in the (thio)phenoxyphenyl phenyl silane composition to be used in making the cured (thio)phenoxyphenyl phenyl polysiloxane composition should be: equal to or greater than 0, at least 0.001, at least 0.1, at least 0.5, or at least 1 ppm; and no more than 500, no more than 200, no more than 100, no more than 50, or no more than 20 ppm, based on the weight of the (thio)phenoxyphenyl phenyl silane composition.

Experimental. Some embodiments of the invention will now be described in detail in the following Examples.

Materials. Most of the siloxane monomers and polymers were purchased from Gelest, Inc. Solvents and other chemicals were purchased from Aldrich or Fisher Scientific. Chemicals were used as received. The platinum concentration is calculated by doing x-ray fluorescence spectroscopy on the platinum stock solutions. Polymer molecular weights are determined by gel-permeation chromatography using polystyrene standards, and are therefore relative molecular weights.

Refractive Index determination. Refractive indices were determined for the silicon-base precursors formed in the following synthetic reaction using a Reichert Abbe Mark II Digital Refractometer.

Procedure for GC-FID analysis. GC-FID analysis was performed on a HP 6890 gas chromatograph with an Agilent Technologies 7683 auto injector. The separation was performed using a 15 M Restek Rtx-5 column with a temperature profile from 100 to 300° C. at 10° C./min. The injection volume was 1.0 µL. The sample was prepared by dissolving 0.10 g of the product (e.g., the produce of Example 1 infra) in approximately 1.0 mL of diethylether. Results are area % results. Due to the similarity of compound compositions, the area % results for the peaks represent good estimates of weight percents (weight % s). Weight percent values are, therefore, equated to area percent values herein.

Accelerated Heat Aging Test. CIE (Commission Internationale de I clairage) analysis of cured (thio)phenoxyphenyl phenyl polysiloxane compositions after heat aging. Samples were cured in a glass microbeaker available from SPI Supplies. The samples were aged in an air oven at 200° C. for the amount of time specified in the examples. The microbeakers have a flat bottom, and generally hold between 0.4 and 1.5 grams of material. The microbeakers have an inner diameter of approximately 18 millimeters so that, when ≧0.4 gram of material is present, an observer can look through a 1.8 cm path length section of material to judge color. In order to measure CIE color of samples, the samples were released from the microbeakers by repeatedly immersing the samples in dry ice, until the siloxane samples had dropped out of the beakers when inverted. The magnitude of the b coordinate depends on the pathlength of the observation. The samples were observed against a calibrated white background and all samples had similar path lengths (~2 millimeters). The samples were analyzed for LAB color using an X-Rite 500 Series Spectrodensitometer. The CIE measurement space was the CIE 1976 Lab space, using a $D_{65}/10$ setting (i.e., 65 degree illumination angle; 10 degree observer angle). A specimen heat aged for 3 days at 200° C. in air which, upon observation using this CIE 1976 Lab space $D_{65}$(illumination angle)/10(observation angle) color test method, has passed the "accelerated heat aging test" if the CIE b value is equal to or less than 2.0. Table 2 contains results of visual inspection.

Accelerated Heat Aging Test. Determination of clarity and color of cured (thio)phenoxyphenyl phenyl polysiloxane compositions by visual inspection. The visual inspections (Table 1) were done using samples in small glass microbeakers (see preparation of samples for CIE Lab test). The samples we viewed edge on through a path length of ~1.8 cm.

Procedure for purification by column distillation of (4-phenoxy-phenyl)-phenyl silanes to purities in excess of 99.9 percent by weight. Several aliquots of the product 4-phenoxy-phenyl phenyl silane (e.g., the 99 weight % pure product of Example 1) were combined into a 500 mL round bottom flask equipped with spin-bar stirrer. Under a pressure of 0.2 mm of Hg, the material was distilled using a 40 tray vacuum insulated column equipped with a thermometer. The distillate was collected once the vapor temperature reached 170 ° C. The product purity (distillation of Example 1 aliquots) was determined to be greater than 99.95 by GC-FID.

EXAMPLE 1.a

Preparation of 4-phenoxy-phenyl phenyl dimethoxy silane using a Grignard based procedure. A 500 mL Schlenk flask was charged with approximately 400 mL of diethylether and 3.3 g (135 mmol) of magnesium (Mg) metal powder and approximately 0.1 mL of methyl iodide. 4-bromodiphenylether (32.161 g, 129 mmol) was added to the flask and the reaction mixture was stirred for 4 hours. Phenyltrimethoxysilane (25.601 g, 129 mmol) was then added to the flask and the contents were stirred for 1 hour. The contents of the Schlenk flask were transferred to a 1 L separatory funnel and the material was washed twice with 400 mL of distilled water. The ether layer was collected and the volatiles were removed under reduced pressure. The purity of the crude product was determined to be 96 area % by GC-FID analysis. Repeated syntheses resulted in crude product purities ranging from 85 to 96 area %. The product was further purified by short path distillation to a purity of 99%. Further purification was achieved by column distillation.

EXAMPLE 1.b

Purification of crude 4-phenoxy-phenyl phenyl dimethoxy silane. Crude 4-phenoxy-phenyl phenyl dimethoxy silane made by the method of Example 1.a. was purified by the method of Example 1.a. to give a purified 4-phenoxy-phenyl phenyl dimethoxy silane containing 97 ppm of p-phenoxyphenyl bromide.

EXAMPLE 2

Preparation of 4-phenoxy-phenyl phenyl dimetboxy silane using a Barbier based procedure. A 1 L Schlenk flask was charged with 800 mL of diethylether and 4.74 g (195 mmol) of Mg powder, approximately 0.1 mL of methyl iodide, 37.564 g (189 mmol) of phenyl trimethoxy silane, and 47.190 g (189.4 mmol) of 4-bromodiphenylether. The contents of the flask were mixed and heated in an ultrasonic bath at 35° C. for 2 hours. The contents of the Schlenk flask were transferred to a 2 L sepratory funnel and the material was washed twice with 400 mL of distilled water. The ether layer was collected and the volatiles were removed under reduced pressure. The purity of the crude product was determined to be 80% by GC-FID analysis. The product was further purified by short path distillation to a purity of 99%. Further purification was achieved by column distillation.

EXAMPLE 3

Preparation of 4-phenoxy-phenyl phenyl dimethoxy silane by lithiation of 4-bromodiphenyl ether. A 500 mL Schlenk flask is charged with 400 mL of diethylether and 30.00 g (120 mmol) of 4-bromodiphenyl ether. The contents of the flask are cooled to −76° C. 75.2 mL (120.4 mmol) of butyl lithium 1.6 M in diethyl ether is added dropwise. The contents of the flask are stirred for 15 minutes. In a 1 L Schlenk flask, a solution of phenyltrimethoxysilane is prepared by dissolving 23.88 g (120 mmol) of phenyltrimethoxysilane in 100 mL of diethylether. By slow addition using a canuula transfer, the contents of the flask containing bromodiphenyl ether are transferred to the flask containing the solution of phenyltrimethoxysilane. The reaction mixture is mixed for 30 minutes and then transferred to a 2 L separatory funnel. The material is washed twice with 400 mL of distilled water. The ether layer is collected and the volatiles are removed under reduced pressure. The purity of the crude product should be 70% as determined by GC-FID analysis. The product is further purified by short path distillation to a purity that should be 99% as determined by GC-FID analysis. Further purification is achieved by column distillation.

EXAMPLE 4

Preparation of phenoxy-phenyl phenyl dimethoxy silane by lithiation diphenyl ether. A 500 mL Schlenk flask is charged with 400 mL of diethylether and 20.50 g (120 mmol) of diphenylether. The contents of the flask are cooled to −76° C. Butyl lithium (75.2 mL, 120 mmol, as a 1.6 M solution in hexanes) is added dropwise. The contents flask is stirred for 15 minutes. In a 1 L Schlenk flask, a solution of phenyltrimethoxysilane is prepared by dissolving 23.88 g (120 mmol) of phenyltrimethoxysilane in 100 mL of diethylether. By slow addition using a canuula transfer, the contents of the flask containing diphenylether are transferred to the flask containing the solution of phenyltrimethoxysilane. The reaction mixture is mixed for 30 min and then transferred to a 2 L separatory funnel. The ether layer was collected and the volatiles were removed under reduced pressure. The purity of the crude product (a mixture of ortho-, meta-, and para-phenoxyphenyl isomers) should be 50% as determined by GC-FID analysis. The product is further purified by short path distillation to a purity that should be 99% as determined by GC-FID analysis. Further purification is achieved by column distillation.

EXAMPLE 5

Preparation of phenoxy-phenyl phenyl dimethoxy silane by palladium catalyzed coupling. A 1 L flask is charged with 400 mL of dimethyl formamide, 30.00 g (120 mmol) of 4-bromodiphenyl ether, and 36,36 g (360 mmol) of triethylamine. A palladium catalyst formed from a mixture of 0.69 g (1.2 mmol) of palladium dibenzylideneacetone, and 1.82 g (6 mmol) of tri-o-tolylphosphine is added to the flask. Phenyldimethoxysilane (20.26 g, 120 mmol) is added to the flask and the contents are heated to 80° C. for 16 hours. The contents of the flask are cooled to room temperature and then filtered. The volatiles are removed under reduced pressure. The concentrated product mixture is dissolved in approximately 400 diethylether and transferred to a 2 L separatory funnel. The material is washed twice with 400 mL of distilled water. The ether layer is collected and the volatiles are removed under reduced pressure. The purity of the extracted and concentrated product should be 80% as determined by GC-FID analysis. The product is further purified by short path distillation to a purity that should be 99% as determined by GC-FID analysis. Further purification is achieved by column distillation.

EXAMPLE 6

Preparation of phenoxy-phenyl phenyl dimethoxy silane by rhodium catalyzed coupling. A 1 L flask is charged with 400 mL of dimethyl formamide, 30.00 g (120 mmol) of 4-bromodiphenyl ether, and 36.36 g (360 mmol) of triethylamine. Rhodium catalyst bis(1,5-cyclooctadiene) rhodium (I) tetrafluoroborate (1.46 g, 3 mol %, 0.004 mol) is added to the flask. Phenyldimethoxysilane (20.26 g, 120 mmol) is added to the flask and the contents are heated to 80° C. for 16 hours. The contents of the flask are cooled to room temperature and then filtered. The volatiles are removed under reduced pressure. The concentrated product mixture is dissolved in approximately 400 diethylether and transferred to a 2 L separatory funnel. The material is washed twice with 400 mL of distilled water. The ether layer is collected and the volatiles are removed under reduced pressure. The purity of the extracted and concentrated product should be 80% as determined by GC-FID analysis. The product is further purified by short path distillation to a purity that should be 99% as determined by GC-FID analysis. Further purification is achieved by column distillation.

Effects of monomer purification on the optical properties of polyphenoxyphenyl(phenyl)siloxanes. It has been found that the purity of phenoxyphenyl phenyl dimethoxysilane employed in the synthesis of poly(phenoxyphenyl)phenylsiloxanes affects the resulting optical properties of the polymers. The affects are illustrated in the following examples.

EXAMPLE 7

Production of water white polymer with sufficiently purified p-phenoxyphenyl phenyl dimethoxy silane.

EXAMPLE 7a

Batch A of p-Phenoxyphenyl phenyl dimethoxy silane. P-Phenoxyphenyl phenyl dimethoxysilane was prepared by the addition of phenyltrimethoxysilane to p-phenoxyphenyl magnesium bromide (Grignard reagent) as described in Example 1. The reaction was worked up as described and remaining phenyltrimethoxysilane and p-phenoxy-phenyl bromide was removed by a single short path distillation. The resulting monomer feedstock had the following composition as determined by GC (area %).

| p-Phenoxyphenyl(phenyl)dimethoxysilane: | 92.62% |
| Phenyltrimethoxysilane: | 6.36% |
| Bromodiphenyl ether: | 0.22% |
| Other peaks: | 0.80% |

EXAMPLE 7b

Batch B of p-Phenoxyphenyl phenyl dimethoxy silane. P-Phenoxyphenyl phenyl dimethoxysilane was prepared by the addition of p-phenoxyphenyl magnesium bromide Grignard reagent to phenyltrimethoxysilane as described in Example 1. The reaction was worked up as described and phenyltrimethoxysilane and p-phenoxy-phenyl bromide was removed by a short path distillation. The monomer was then distilled through a short path distillation head a second time. The resulting monomer feedstock had the following composition as determined by GC:

| p-Phenoxyphenyl(phenyl)dimethoxysilane: | 98.92% |
| Phenyltrimethoxysilane: | 0.087% |
| Bromodiphenyl ether: | 0.064% |
| Other peaks: | 0.92% |

EXAMPLE 7c

Polymerization of p-phenoxyphenyl phenyl dimethoxy silane from Batch A monomer (yellow product) and Batch B monomer (colorless product). Two identical polymerizations were conducted with Batch A and B of p-phenoxyphenyl phenyl dimethoxy silane monomer. P-phenoxyphenyl phenyl dimethoxy silane (18.47 grams), 21.10 grams of diphenyl dimethoxy silane, 2.93 grams of divinyl tetramethyl disiloxane were mixed together to form a solution. The mixture was added to a 100 mL 3-necked round bottom flask equipped with a heating mantle, magnetic stirrer, thermometer and condenser. Water (6.65 grams) and 3.06 grams of tetrabutyl ammonium hydroxide were then added to the reaction mixture. The reaction was heated until refluxing was observed (~77-80° C. pot temperature). The reaction was carried out in reflux mode for 1 hour. The reflux condenser was then removed and a stream of nitrogen was blown into the reaction mixture to remove methanol and water. The nitrogen sparge was carried out for 1 hour. At the end of the nitrogen sparge, the reaction pot temperature was 90° C. The reaction was cooled to room temperature and 100 mL of toluene were added. The resulting mixture was washed 3 times with 200 mL of 5% HCl and then 2 times with 250 mL of water. The toluene-siloxane phase was then dried with 5 grams of anhydrous magnesium sulfate and filtered through filter paper. The toluene-siloxane solution was then stripped on a rotary evaporator under high vacuum and 85° C. For Batch A monomer, 32 grams of a clear but yellowish product was obtained. For Batch B monomer, 31 grams of a crystal clear water white material was obtained.

EXAMPLE 8

Effect of p-phenoxy-phenyl bromide on Heat Aging of Poly(p-Phenoxyphenyl)phenylsiloxanes at 200° C. in Air. Poly(phenoxyphenyl)phenylsiloxanes are useful as encapsulants for solid-state LEDs if they can tolerate conditions of high heat for thousands of hours. The encapsulants can be exposed to junction temperatures of 120-150° C. when used in solid-state LEDs. An accelerated heat aging test consisting of aging poly(phenoxyphenyl)phenylsiloxane formulations in a 200° C. oven in air has been developed to predict aging properties over the 50,000 hour lifetimes during which many LED devices operate. The following formulations illustrate the effect of residual p-bromodiphenyl ether impurities in the poly(p-phenoxyphenyl)phenylsiloxanes. The formulations contain Polymer A (a vinyl-containing p-phenoxyphenyl phenyl polymer after distillation through a 40 tray column under vacuum twice, so that residual p-phenoxy-phenyl bromide was 97 ppm in the monomer as determined by GC), Polymer B (a commercially available silicone hydride), Platinum catalyst for hydrosilation (the effects of Pt on color generation are discussed in U.S. provisional patent application 60/851,945), and varying amounts of p-bromodiphenyl ether. Polymer B was HPM-502 from Gelest, poly(methylhydrosiloxane-co-phenylmethylsiloxane), dimethylsilyl-terminated. The hydride equivalents in Polymer B were 196 grams/equivalent of Si—H bonds as determined by NMR. The platinum catalyst was Ossko catalyst, platinum carbonyl cyclovinylmethylsiloxane complex in vinylmethylcyclosiloxanes, used as supplied from Gelest. X-ray fluorescence measurements showed the Gelest solution was 20850 ppm in elemental platinum. For the formulations below, the Pt solution was diluted 100-fold with xylenes for dispensing. The p-phenoxy-phenyl bromide was used as received from Aldrich.

EXAMPLE 8a

Polymer A Synthesis. The high purity p-phenoxyphenyl phenyl dimethoxy silane monomer used in this example was distilled through a 40 tray column under vacuum twice, so that residual p-phenoxy-phenyl bromide was 97 ppm in the monomer as determined by GC. Diphenyl Dimethoxysilane (19.94 g., 0.082 mol, 51 mol %), dimethoxy-(4-phenoxyphenyl)-phenyl-silane (18.29 g., 0.054 mol, 34 mol % ), and divinyltetramethyl disiloxane (4.47 g., 0.024 mol, 15 mol %, making 100 mol % total of monomers) were added to a 100 mL round bottom two neck flask ("Flask A") with a Teflon stir bar. Deionized water (4.51 g., 0.251 mol, 158 mol %) and tetrabutylammonium hydroxide, 40 wt/% in water (2.07 g., 0.0032 mol, 2 mol %) were combined in a vial and then the contents of the vial were added to Flask A. A short path distillation head was placed in one of the necks of Flask A and a thermocouple was placed in the other to monitor the reaction temperature. A heating mantle was used as the heating source for Flask A and a controller was used to regulate the temperature. A thermometer was used to measure the distillate temperature. Flask A was heated and stirred at 85° C. for 1 hr. 30 min. and 8.52 g. of distillate was collected. The contents in Flask A were heated at 80° C. for an additional 1 hr. and 10 min. in reflux mode. Approximately 150 mL of toluene was added to the contents of Flask A. The contents of Flask A were then transferred to a separation flask ("Flask B") and the contents were washed with 150 mL of 5% HCl solution. The aqueous phase was discarded and the organic phase was washed 2 more times with 150 mL of 5% HCl solution and 2 times with 150 mL of Deionized Water. The organic layer was then dried with anhydrous magnesium sulfate overnight and then the magnesium sulfate was removed using filtration. The toluene was removed by rotory evaporation under house vacuum using a 80-90° C. water bath as a heat source during 1 hour. The polymer yield was 29.60 g (81.3% yield). NMR indicated that polymer A contained 1342 g/mol of vinyl groups.

EXAMPLE 8b

Formulations having varying amounts of p-phenoxy-phenyl bromide. The formulations were prepared as follows. Polymer A was mixed with the appropriate amount of Pt catalyst using a stir-bar at 80° C. Polymer B and the p-phenoxy-phenyl bromide were then added at room temperature, followed by vigorous stirring at 80° C. using a stir bar. The formulations were prepared in glass microbeakers, containing approximately 0.5 grams of material. The formulations were set in an oven at 150° C. for 18 hours. All of the samples were visually observed to be transparent and water white. The samples were then placed in a 200° C. oven and aged. Tables 1 and 2 show the formulations and results. In the CIE Lab color scale, it has been found that the b value tracks closely with the amount of yellow/brown present in samples. The magnitude of the b coordinate depends on the path length of the observation. The samples (Table 2) were observed against a calibrated white background, and all samples had similar path lengths (~2 mm). The visual inspections (Table 1) were done using samples in small glass microbeakers, and the path length was ~1.8 cm. The results recorded in Table 1 indicate that, by visual inspection through a pathlength of ~18 millimeters, samples containing added p-phenoxy-phenyl bromide at levels of 0, 500, and 1,000 ppm, based on the phenoxyphenyl phenyl vinyl silicon-based precursor, remain clear and colorless after 1 day at 200° C. in air. After three days at at 200° C. in air, the samples containing 500 ppm and 1,000 ppm of added p-phenoxy-phenyl bromide display, respectively, very slight and slight yellow color. The results recorded in Table 2 indicate that CIE b-values (path length ~2 mm) for samples containing added p-phenoxy-phenyl bromide at levels of 0, 500, and 1,000 ppm, based on the phenoxyphenyl phenyl vinyl silicon-based precursor, retain DIE Lab b-values in the "pass" range (i.e., below a value of 2.0) after 3 day at 200° C. in air.

TABLE 1

Formulations showing the effect of p-phenoxy-phenyl bromide impurities on heat aging in phenoxyphenyl siloxanes as observed by visual inspection.

| Label | Phenoxyphenyl phenyl vinyl silicon-based precursor | Silicon Hydride | Si—H:vinyl Equivalent Ratio | Pt level (ppm) | p-phenoxy-phenyl bromide added[a] (ppm) | Color by visual inspection[b] after a time interval (days) at 200° C. (path length ~18 mm) | |
|---|---|---|---|---|---|---|---|
| | | | | | | 1 day | 3 days |
| A | Polymer A | Polymer B | 2 | 0.5 | 0 | CC | CC |
| B | Polymer A | Polymer B | 2 | 0.5 | 500 | CC | VSY |

TABLE 1-continued

Formulations showing the effect of p-phenoxy-phenyl bromide impurities on heat aging in phenoxyphenyl siloxanes as observed by visual inspection.

| Label | Phenoxyphenyl phenyl vinyl silicon-based precursor | Silicon Hydride | Si—H:vinyl Equivalent Ratio | Pt level (ppm) | p-phenoxy-phenyl bromide added[a] (ppm) | Color by visual inspection[b] after a time interval (days) at 200° C. (path length ~18 mm) 1 day | 3 days |
|---|---|---|---|---|---|---|---|
| C | Polymer A | Polymer B | 2 | 0.5 | 1000 | CC | SY |
| D | Polymer A | Polymer B | 2 | 0.5 | 5000 | Y | B |

[a]Approximately 44 ppm was already present due to the starting reaction mixture.
[b]Descriptive abbreviations for sample appearance: CC=clear colorless; B=brown; Y=yellow; SY=slightly yellow; VSY=very slightly yellow

TABLE 2

Formulations showing the effect of p-phenoxy-phenyl bromide impurities on heat aging in phenoxyphenyl siloxanes as observed using the Hunter L*ab color test.

| Label | Phenoxyphenyl phenyl vinyl silicon-based precursor | Silicon Hydride | Si—H:vinyl Equivalent Ratio | Pt level (ppm) | p-phenoxy-phenyl bromide added[a] (ppm) | L, a, b color after after a time interval of 3 days at 200° C. (path length ~2 mm) |
|---|---|---|---|---|---|---|
| A | Polymer A | Polymer B | 2 | 0.5 | 0 | 50.25, −1.06, −0.18 |
| B | Polymer A | Polymer B | 2 | 0.5 | 500 | 49.16, −1.26, 0.40 |
| C | Polymer A | Polymer B | 2 | 0.5 | 1000 | 51.63, −1.27, 0.75 |
| D | Polymer A | Polymer B | 2 | 0.5 | 5000 | 53.61, −1.55, 23.66 |

[a]Approximately 44 ppm was already present due to the starting reaction mixture.

We claim:

1. A (thio)phenoxyphenyl phenyl silane composition comprising a (thio)phenoxyphenyl phenyl silane having Formula I $$Ph^2\text{-}Q\text{-}Ph^1\text{-}Si(Ph^3)(OR)_2 \quad (I)$$

wherein:
- $Ph^1$ is a phenyl ring having $Ph^2$-Q-, —Si($Ph^3$)(OR)$_2$, and four hydrogen atoms as substituents;
- $Ph^2$-Q is a (thio)phenoxy group where $Ph^2$ is phenyl and Q is selected from oxygen atom, sulfur atom, and combinations thereof;
- $Ph^2$-Q is in a position on the $Ph^1$ phenyl ring which is ortho-, meta-, or para-relative to the Si atom;
- $Ph^3$ is phenyl; and
- R is independently selected from: a hydrogen atom, a $C_1$-$C_{10}$ hydrocarbon radical, and combinations thereof,
  wherein the $C_1$-$C_{10}$ hydrocarbon radical is independently selected from:
    linear, branched, or cyclic $C_1$-$C_{10}$ alkyl; phenyl; substituted phenyl; aralkyl; and combinations thereof; and
  wherein the (thio)phenoxyphenyl phenyl silane is present in the composition in an amount of at least 99.0 percent by weight to less than or equal to 100 percent by weight, based upon the weight of the (thio)phenoxyphenyl phenyl silane composition.

2. The (thio)phenoxyphenyl phenyl silane composition of claim 1, wherein R is selected from hydrogen atom, methyl, and ethyl.

3. The (thio)phenoxyphenyl phenyl silane composition of claim 1, further comprising a (thio)phenoxyphenyl halide having Formula II $$Ph^2\text{-}Q\text{-}Ph^1\text{-}X \quad (II)$$

wherein:
- $Ph^1$ is a phenyl ring having $Ph^2$-Q-, X and four hydrogen atoms as substituents;
- $Ph^2$-Q is a (thio)phenoxy group where $Ph^2$ is phenyl and Q is selected from oxygen atom, sulfur atom, and combinations thereof;
- $Ph^2$-Q is in a position on the $Ph^1$ phenyl ring which is ortho-, meta-, or para-relative to the X; and
- X is a halide selected from Cl, Br, and combinations thereof; and
wherein the (thio)phenoxyphenyl halide is present in an amount of at least 0.001 ppm and no more than 500 ppm, based on the weight of the (thio)phenoxyphenyl phenyl silane composition.

4. The (thio)phenoxyphenyl phenyl silane composition of claim 1, wherein the (thio)phenoxyphenyl phenyl silane composition is free of any (thio)phenoxyphenyl halide having Formula II $$Ph^2\text{-}Q\text{-}Ph^1\text{-}X \quad (II)$$

wherein:
- $Ph^1$ is a phenyl ring having $Ph^2$-Q-, —X and four hydrogen atoms as substituents;
- $Ph^2$-Q is a (thio)phenoxy group where $Ph^2$ is phenyl and Q is selected from oxygen atom, sulfur atom, and combinations thereof;
- $Ph^2$-Q is in a position on the $Ph^1$ phenyl ring which is ortho-, meta-, or para-relative to the X; and
- X is a halide selected from Cl, Br, and combinations thereof.

5. A method of making the (thio)phenoxyphenyl phenyl silane composition of claim 1, comprising the steps of:

A. providing a (thio)phenoxyphenyl halide having Formula II $$Ph^2\text{-}Q\text{-}Ph^1\text{-}X \quad (II)$$

wherein:
- $Ph^1$ is a phenyl ring having $Ph^2$-Q-, X and four hydrogen atoms as substituents;
- $Ph^2$-Q is a (thio)phenoxy group where $Ph^2$ is phenyl and Q is selected from oxygen atom, sulfur atom, and combinations thereof;
- $Ph^2$-Q is in a position on the $Ph^1$ phenyl ring which is ortho-, meta-, or para-relative to X; and
- X is a halide selected from Cl, Br, and combinations thereof;

B. providing a phenyl trioxy silane having Formula III $$Ph^3\text{-}Si(OR)_2(OR') \quad (III)$$

wherein:
- each R is a hydrogen atom or a $C_1$-$C_{10}$ hydrocarbon radical independently selected from: linear, branched, or cyclic $C_1$-$C_{10}$ alkyl; phenyl; substituted phenyl; aralkyl; and combinations thereof; and
- R' is a $C_1$-$C_{10}$ hydrocarbon radical independently selected from: linear, branched, or cyclic $C_1$-$C_{10}$ alkyl; phenyl; substituted phenyl; aralkyl; and combinations thereof;

C. reacting the (thio)phenoxyphenyl halide with an active metal reagent comprising metal atom M to form a (thio)phenoxyphenyl metal intermediate having formula IV $$Ph^2\text{-}Q\text{-}Ph^1\text{-}M\text{-}X_n \quad (IV)$$

wherein:
- M is selected from magnesium and lithium;
- X is selected from Cl, Br, and combinations thereof; and
- n=0 or 1; and D. reacting the (thio)phenoxyphenyl metal intermediate with the phenyl trioxy silane to form the (thio)phenoxyphenyl phenyl; and E. purifying the (thio)phenoxyphenyl phenyl silane.

6. The method of claim 5, wherein the step of purifying produces the (thio)phenoxyphenyl phenyl silane composition comprising the phenoxyphenyl phenyl silane in an amount of at least 99.0 weight percent to less than or equal to 100 weight percent, based on the weight of the (thio)phenoxyphenyl phenyl silane composition.

7. The method of claim 5, wherein the step of purifying produces the (thio)phenoxyphenyl phenyl silane composition, wherein the (thio)phenoxyphenyl halide is present in an amount of equal to or greater than 0 ppm and no more than 500 ppm, based on the weight of the phenoxyphenyl silane composition.

* * * * *